United States Patent
Muthusamy et al.

(10) Patent No.: US 10,752,567 B2
(45) Date of Patent: Aug. 25, 2020

(54) METHOD FOR ACID TREATMENT CONDITIONING OF A CATALYST IN THE PRODUCTION OF GLYCOLS

(71) Applicant: SHELL OIL COMPANY, Houston, TX (US)

(72) Inventors: Duraisamy Muthusamy, Houston, TX (US); Viet Quoc Nguyen, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/336,140

(22) PCT Filed: Sep. 28, 2017

(86) PCT No.: PCT/US2017/053862
§ 371 (c)(1),
(2) Date: Mar. 25, 2019

(87) PCT Pub. No.: WO2018/064245
PCT Pub. Date: Apr. 5, 2018

(65) Prior Publication Data
US 2019/0256446 A1    Aug. 22, 2019

Related U.S. Application Data

(60) Provisional application No. 62/401,410, filed on Sep. 29, 2016.

(51) Int. Cl.
| | | |
|---|---|---|
| C07C 29/00 | (2006.01) | |
| B01J 25/00 | (2006.01) | |
| B01J 31/00 | (2006.01) | |
| C07C 29/132 | (2006.01) | |
| B01J 25/02 | (2006.01) | |
| B01J 31/04 | (2006.01) | |
| C07C 31/20 | (2006.01) | |

(52) U.S. Cl.
CPC ............ *C07C 29/132* (2013.01); *B01J 25/02* (2013.01); *B01J 31/04* (2013.01); *C07C 31/202* (2013.01)

(58) Field of Classification Search
CPC .......... B01J 25/02; B01J 31/04; C07C 29/132
See application file for complete search history.

(56) References Cited

U.S. PATENT DOCUMENTS 3,657,157 A    4/1972  Pieters et al.

FOREIGN PATENT DOCUMENTS

WO    2015154258 A1    10/2015

OTHER PUBLICATIONS

International Search Report and Written Opinion received for PCT Patent Application No. PCT/US2017/053862, dated Dec. 22, 2017, 9 pages.

*Primary Examiner* — Sikarl A Witherspoon (57) ABSTRACT

Implementations of the disclosed subject matter provide methods for producing ethylene glycol from a carbohydrate feed which may include conditioning a heterogeneous hydrogenation catalyst by treatment with a protic acid resulting in an acid-conditioned heterogeneous hydrogenation catalyst. Next, in a reactor under hydrogenation conditions, the carbohydrate feed may be contacted with a bi-functional catalyst system comprising the acid-conditioned heterogeneous hydrogenation catalyst, and a soluble retro-Aldol catalyst. An intermediate product stream may be obtained from the reactor including ethylene glycol.

10 Claims, 2 Drawing Sheets

METHOD FOR ACID TREATMENT CONDITIONING OF A CATALYST IN THE PRODUCTION OF GLYCOLS

CROSS-REFERENCE TO RELATED APPLICATIONS

This is a national stage application of International Application No. PCT/US2017/053862, filed 28 Sep. 2017, which claims benefit of priority to U.S. Provisional Application No. 62/401,410, filed 29 Sep. 2016.

TECHNICAL FIELD OF THE INVENTION

The present invention relates to a process for converting a carbohydrate feed stock into glycols. More specifically the present invention relates to a process for preparing glycols, particularly ethylene glycol and propylene glycol, by converting a carbohydrate feed stock material in a reactor using a bi-functional catalyst system including a heterogeneous hydrogenation catalyst which is subjected to an acid-treatment conditioning step.

BACKGROUND

Glycols such as ethylene glycol and propylene glycol are valuable materials with a multitude of commercial applications, e.g. as heat transfer media, antifreeze, and precursors to polymers, such as PET. The market for ethylene and propylene glycols (EG and PG) is expanding worldwide, with the EG market being vastly bigger than the market for PG (i.e., 1,2-propylene glycol). Ethylene and propylene glycols are typically made on an industrial scale by hydrolysis of the corresponding alkylene oxides, which are the oxidation products of ethylene and propylene, produced from fossil fuels/petrochemical feed stocks involving multiple processing steps. Use of bio-based feed stocks for the production of energy and chemicals has become increasingly desirable in the industry since this approach to use feeds from renewable sources provides a pathway for sustainable development.

In recent years, increased efforts have focused on producing chemicals, including glycols, from renewable feedstocks, such as carbohydrate-containing feedstock. Carbohydrates are plentiful and renewable bio-mass feeds having the structural features resembling that of ethylene glycol; each carbon has one attached hydroxyl group or contains an oxygen function that can be readily converted into a hydroxyl. As such, EG and PG can be produced if the C-C bonds are selectively cleaved into $C_2$ and $C_3$ units.

As with many chemical processes, the reaction product stream in these processes comprises a number of desired materials as well as diluents, by-products and other undesirable materials. In order to provide a high value process, the desirable product or products must be obtainable from the reaction product stream in high purity with a high percentage recovery of each product and with as low as possible use of energy, chemical components and complex equipment. In addition, the catalysts used in the process should allow for the selective formation of ethylene glycol over the other glycols, high yields of the total glycols mixture, use of a high-concentration sugar solution as feed to the reactor, and maintain stable catalyst activity over time. These desirable features are challenging to achieve, particularly considering the instability of the catalysts under the process conditions.

Therefore, it would be advantageous to provide an improved method suitable for the production of glycols from carbohydrate feeds including a technique to improve the catalyst performance in the process in order to make the overall glycol production process more economical than processes disclosed previously in the industry.

BRIEF SUMMARY

According to an embodiment of the disclosed subject matter, a method for producing ethylene glycol from a carbohydrate feed which may include conditioning a heterogeneous hydrogenation catalyst by treatment with a protic acid resulting in an acid-conditioned heterogeneous hydrogenation catalyst. Next, in a reactor under hydrogenation conditions, the carbohydrate feed may be contacted with a bi-functional catalyst system comprising the acid-conditioned heterogeneous hydrogenation catalyst, and a soluble retro-Aldol catalyst. An intermediate product stream may be obtained from the reactor including ethylene glycol.

Implementations of the disclosed subject matter provide an improved method for producing ethylene glycol from a carbohydrate feed. Because the disclosed subject matter achieves improved catalyst performance, the process results in the selective formation of ethylene glycol over the other glycols, high yields of the total glycols mixture, use of a high-concentration sugar solution as feed to the reactor, while maintaining stable catalyst activity over time. Therefore, the disclosed subject matter provides an improved method suitable for the production of glycols from carbohydrate feeds including a catalyst acid conditioning technique to improve the catalyst performance in the process in order to make the overall glycol production process more economical than processes disclosed previously in the industry.

Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Carbohydrates are readily available and renewable biomass feeds, and they have the structural features resembling that of ethylene glycol; each carbon has one attached hydroxyl group or contains an oxygen function that can be readily converted into a hydroxyl. Ethylene glycol (EG) and propylene glycol (PG) can be produced by selectively cleaving the C—C bonds into $C_2$ and $C_3$ units. As such, the presently disclosed subject matter provides a process for the conversion of carbohydrate feed stock materials and hydrogen gas into glycols, particularly with ethylene glycol as the main product and propylene glycol as a smaller co-product.

The process variables have major impacts on the conversion and selectivity of the reaction. For example, the particular catalyst(s) used and process conditions can provide for a successful reaction selectivity outcome under a set of practical reaction conditions. Examples of process variables include feed stock (e.g., sucrose, glucose, sorbitol, $C_5$ versus $C_6$ sugars, starch, and the like); one or more catalysts (e.g., having retro-Aldol and hydrogenation functions); temperature, catalyst performance and stability, $H_2$ partial pressure, $H_2$/feed ratio, residence time, reaction medium (e.g., a solvent such as water), pH in the reaction medium, and feed/solvent ratio. According to the presently disclosed subject matter, the catalyst performance and long-term stability are identified as being particularly important taking into consideration the chemistry of the reaction discussed below.

The sugars to glycols hydrogenolysis reaction, which is carried out using a metal catalyst and in the presence of hydrogen, is a complex reaction known to produce hundreds of products. Since ethylene and propylene glycols are the desired products, the other products must be minimized by selecting the appropriate catalyst and conditions; additionally an EG/PG wt % ratio of at least 1:1 and preferably 7:1 or more is desirable. In general, sugars tend to cleave into $C_3$ fragments more easily than the desired $C_2$ fragment, resulting in the formation of propylene glycol as the single most predominant molecule.

While the selection of the most appropriate catalyst, not only from the selectivity point of view but also from the point of view of catalyst longevity, is an important task, other aspects of the reaction must also be considered. The catalyst generally only controls the chemistry taking place on its surface; for example, the cleavage of the sugar molecules into smaller fragments taking place by discrete retro-Aldol reactions followed by hydrogenation of the intermediates into products is the desired pathway. However, quite a number of other reactions take place in solution and these side reactions must also be considered. A number of ions such as OH—, OAc-, etc. could be present in the solution under basic pH conditions or H+ ions could be present under acidic pH conditions. While these ions could also catalyze the retro-Aldol reaction, these ions are generally known to catalyze a variety of dehydration side-reactions causing the sugar molecules to degrade into wasteful products. These undesirable side reactions could become dominant particularly under high temperature conditions. A proper choice of catalysts and process conditions is therefore essential in order to realize the objectives of high glycol yields and long catalyst life. Multiple equations can be used to explain the various steps of the chemistry of the conversion of sugars to EG and PG, as shown below.

Starch

Glucose

Sorbitol

Erthtitol

Erthtitol Glycol

As shown above, the chemistry of sugars in the hydrogenolysis reaction is a notoriously complex set of functional group chemistries; the products from any reaction could be reactants for all other reactions, including those taking place on the surface of the solid catalyst. The product distribution (EG, PG, partially converted sugars, etc.) at the end of reaction will be a function of the relative rates of these reactions under the chosen experimental conditions. Thus, according to the presently disclosed subject matter, important process variables including catalyst performance and stability have been improved for the disclosed method for producing ethylene glycol from a carbohydrate feed.

The presently disclosed method for producing ethylene glycol from a carbohydrate feed has numerous advantages over the prior art. The catalyst conditioning step and bifunctional catalyst system used in the presently disclosed process allows for the selective formation of ethylene glycol over the other glycols, high yields of the total glycols mixture, use of a high-concentration sugar solution as feed to the reactor, and maintains stable catalyst activity over time.

The presently disclosed catalyst conditioning acid treatment technique improves the catalyst performance in the process in order to make the overall glycol production process more economical than processes disclosed previously in the industry. As a result, the presently disclosed method has the advantages of achieving high total glycol yield, high EG:PG ratio, and maintaining a stable catalyst system for at least 24 hours, at least 50 hours, and at least 100 hours.

According to an implementation of the disclosed subject matter, a method for producing ethylene glycol from a carbohydrate feed may include conditioning a heterogeneous hydrogenation catalyst by treatment with a protic acid resulting in an acid-conditioned heterogeneous hydrogenation catalyst. Next, in a reactor under hydrogenation conditions, the carbohydrate feed may be contacted with a bi-functional catalyst system comprising the acid-conditioned heterogeneous hydrogenation catalyst, and a soluble retro-Aldol catalyst. An intermediate product stream may be obtained from the reactor including ethylene glycol.

In an embodiment, the protic acid may be at least one of an organic acid, a mineral acid, and combinations thereof. Examples of organic acids suitable for use in the catalyst conditioning step are formic acid, acetic acid, propionic acid, butyric acid, glycolic acid, lactic acid, citric acid, benzoic acid, and combinations thereof. According to an embodiment, the organic acid may be at least one of lactic acid, glycolic acid, and combinations thereof. Examples of mineral acids suitable for the catalyst conditioning step are dilute solution of HCl, $H_2SO_4$, $H_3PO_4$, benzene sulfonic acid, and combinations thereof. However, when a mineral acid is used, the residual acids must be completely removed from the catalyst before using the catalyst in the sugars to glycols conversion process.

A range of protic acid concentrations may be employed for the catalyst conditioning step. The protic acid concentration may be in the range of from about 0.001 wt % to about 50 wt %, from about 0.01 wt % to about 10 wt %, and from about 0.1 wt % to about 1 wt % range. In an embodiment, the conditioning step may be carried out with a concentration of protic acid in the range of from about 0.001 wt % to about 50 wt %.

According to an embodiment, the conditioning step may be carried out with an acid solution solvent. Examples of the acid solution solvent include $H_2O$, alcohol, and combinations thereof. In an embodiment, the acid solution solvent may be $H_2O$.

The conditioning step may be carried out under variable conditions. In an embodiment, the conditioning step may be carried out under hydrogen atmosphere. The hydrogen partial pressure may range from about 15 psia to about 5000 psia, from about 15 psia to about 3000 psia and from about 500 psia to about 1500 psia. In an embodiment, the conditioning step may be carried out at a pressure in the range of from about 15 psia to about 5000 psia. The temperature used for the conditioning step may be in the range of from about 25° C. to about 350° C., from about 100° C. to about 275° C., and from about 200° C. to about 250° C. In an embodiment, the conditioning step may be carried out at a temperature in the range of from about 25° C. to about 350° C.

The reaction time suitable for the conditioning step may be in the range of from about 0.1 hours to about 100 hours, from about 1 hour to about 50 hours, and from about 12 hours to about 36 hours. In an embodiment, the conditioning step may be carried out for a reaction time of from 0.1 hours to about 100 hours.

Examples of heterogeneous hydrogenation catalysts suitable for the conditioning step are supported and un-supported metal catalysts selected from Group 8 to Group 11 metals in the periodic table. Examples of un-supported metal catalysts are Raney-metal catalysts such as Raney-Ni, Raney-Co, Raney-Cu, and Raney-Ru, and metal-powder catalysts such as powdered Ni, Co, Cu, Cu—Zn, Cu—Cr, Ni—Mo, Ni—W, and Ni—Cr. The heterogeneous hydrogenation catalyst may be promoted with metals such as Al, Fe, Cr, Mn, Co, Cu, Mo, Ru, Rh, Pd, Ag, W, Re, Ir, Pt, Au, In, Sn, Sb, and Pb. One or more metals may be used in the formulation of the promoted metal catalysts. The promoting metals may be present in concentrations ranging from about 0.001 wt % to about 10 wt %. Examples of supported-metal hydrogenation catalysts are Group 8 to Group 11 metal catalysts supported on hydrothermally stable supports such as $TiO_2$, $ZrO_2$, and alpha-alumina. The metals may be used individually or in combination with one or more of the other metals.

The carbohydrate feed for the process may include one or more of glucose, sucrose, xylose, sugar cane molasses, starch (e.g., hydrolyzed starch, corn syrup, and the like), and cellulose (e.g., hydrolyzed cellulose, and the like). In an embodiment, the carbohydrate feed may include a concentration of carbohydrate, in the total solution entering the reactor of 5-40 wt % in a solvent, at least 5 wt % in a solvent, and at least 10 wt % in a solvent.

The reaction solvent may be water, a $C_1$ to $C_6$ alcohol, a $C_1$ to $C_6$ polyol, or mixtures thereof. Further solvent may also be added to the reactor in a separate feed stream or may be added to the carbohydrate feed before it enters the reactor. Examples of $C_1$ to $C_6$ polyols include 1,2-hexanediol, glycerol, etc. As an example, the reaction solvent may be a mixture including $H_2O$ and at least one of alcohols, ethers, and ether-alcohols, and mixtures thereof. In an embodiment, the reaction solvent may be $H_2O$.

Suitable reactor vessels to be used in the process of the preparation of ethylene glycol from a carbohydrate feed include continuous stirred tank reactors (CSTR), plug-flow reactors, slurry reactors, ebbulated bed reactors, jet flow reactors, mechanically agitated reactors, back-mixed reactors, bubble columns, such as slurry bubble columns and external recycle loop reactors. The use of these reactor vessels allows dilution of the reaction mixture to an extent that provides high degrees of selectivity to the desired glycol product (mainly ethylene and propylene glycols). There may be one or more of such reactor vessels, arranged in series. In one embodiment, preferably there are two reactor vessels arranged in series, the first one of which is a CSTR, the output of which is supplied into a plug-flow reactor.

The disclosed method for producing ethylene glycol from a carbohydrate feed may be performed under particular hydrogenation conditions in order to maximize the desired yield of EG. For example, the hydrogenation conditions may include temperature, pressure, flow rate, and any other process variable that may be controlled. In an embodiment, the hydrogenation conditions may include a temperature in the range of from 180-250° C. and from 210-250° C. The hydrogenation conditions may also include a pressure in the range of from 500 to 2000 psig.

In an embodiment, the presently disclosed method may also include contacting the carbohydrate feed with hydrogen. For example, the disclosed method may take place in the presence of hydrogen. Hydrogen may be supplied into the reactor vessel under pressure in a manner common in the art. Hydrogen is supplied into the reactor vessels under pressure. In an example, the method of the present reaction takes place in the absence of air or oxygen. In order to achieve this, it is preferable that the atmosphere in the reactor vessel be evacuated and replaced with hydrogen repeatedly, after loading of any initial reactor vessel contents, before the reaction starts.

According to an embodiment, the bi-functional catalyst system may include the acid-conditioned heterogeneous hydrogenation catalyst, and a soluble retro-Aldol catalyst. The soluble retro-Aldol catalyst may comprise one or more compounds, complex or elemental material comprising tungsten, molybdenum, vanadium, niobium, chromium, titanium or zirconium. In particular, the soluble retro-Aldol catalyst may comprise one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. According to an embodiment, examples of the soluble retro-Aldol catalyst may include at least one of: silver tungstate, sodium metatungstate, ammonium meta-tungstate, sodium poly-tungstate, tungstic acid, alkali- and alkaline-earth metal tungstates, sodium phospho-tungstate, phospho-tungstic acid, alkali- and alkaline-earth metal phospho-tungstates, alkali- and alkaline-earth metal molybdates, alkali- and alkaline-earth metal phospho-molybdates, phospho-molybdic acid, heteropoly acids, mixed tungstates and molybdates, niobic acid, silicotungstic acid, alkali- and alkaline-earth metal niobates.

According to an embodiment, at least one of the acid-conditioned heterogeneous hydrogenation catalyst and soluble retro-Aldol catalyst of the bi-functional catalyst system is supported on a solid support. In an embodiment, any other active catalyst component may be present in either heterogeneous or homogeneous form. In this case, any other active catalyst component may also be supported on a solid support. In one embodiment, the heterogeneous hydrogenation catalyst is supported on one solid support and the soluble retro-Aldol catalyst is supported on a second solid support which may comprise the same or different material.

As a specific example, the heterogeneous hydrogenation catalyst may be a hydrogenation catalyst supported on a hydrothermally stable support. In another embodiment, both the heterogeneous hydrogenation catalyst and soluble retro-Aldol catalyst are supported on one solid hydrothermally stable support.

The solid support may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

In an embodiment, the disclosed method may also include running the reaction under pH controlled conditions. In particular, the pH of the reaction may be in the range of from 2-7. The pH may be controlled using at least one pH controlling agent such as alkali- and alkaline-earth metal salts of carbonic acid or carboxylic acids or combinations thereof, alkali- and alkaline-earth metal salts of phosphoric acid, zinc carbonate, and zinc salts of carboxylic acids.

According to the presently disclosed subject matter, an intermediate product stream may be obtained from the reactor including ethylene glycol. The intermediate product stream may include at least 5 wt % concentration of glycols. In addition, the intermediate product stream may include a yield of at least 60 wt % glycols, and at least 70 wt % glycols. In an embodiment, the intermediate product stream may include a yield of at least 60 wt % EG, and at least 65 wt % EG. An advantage of the presently disclosed method is the ability to maximize the yield of EG relative to the yield of PG. For example, the intermediate product stream may include an EG/PG wt % yield ratio of at least 1:1, a EG/PG wt % yield ratio of at least 7:1, and a EG/PG wt % yield ratio of at least 10:1. In addition, the presently disclosed method allows for minimizing undesired products of the subject reaction. Accordingly, the intermediate product stream may include a yield of no more than 10 wt % sorbitol. Further, the intermediate product stream may include a yield of less than 3 wt % 1,2-butanediol. Additionally, the product stream may include a minimum EG/1,2BDO wt % yield ratio of 20:1, thereby maximizing the EG yield relative to other less desired products.

According to an embodiment, the intermediate product stream may be further processed. For example, the intermediate product stream may be fed to a second reactor which may include contacting the intermediate product stream from the first reactor with hydrogen in the presence of a heterogeneous hydrogenation catalyst. A final product stream comprising ethylene glycol may be obtained that is substantially free of compounds containing carbonyl functional groups. The heterogeneous hydrogenation catalyst used in this further processing of the intermediate product stream may or may not be the same heterogeneous hydrogenation catalyst used in the bi-functional catalyst system in the glycols production process. In addition, prior to this further processing step, the heterogeneous hydrogenation catalyst may be subjected to a catalyst conditioning step comprising treatment of the heterogeneous hydrogenation catalyst with protic acid in the presence of hydrogen atmosphere.

Figure 1:
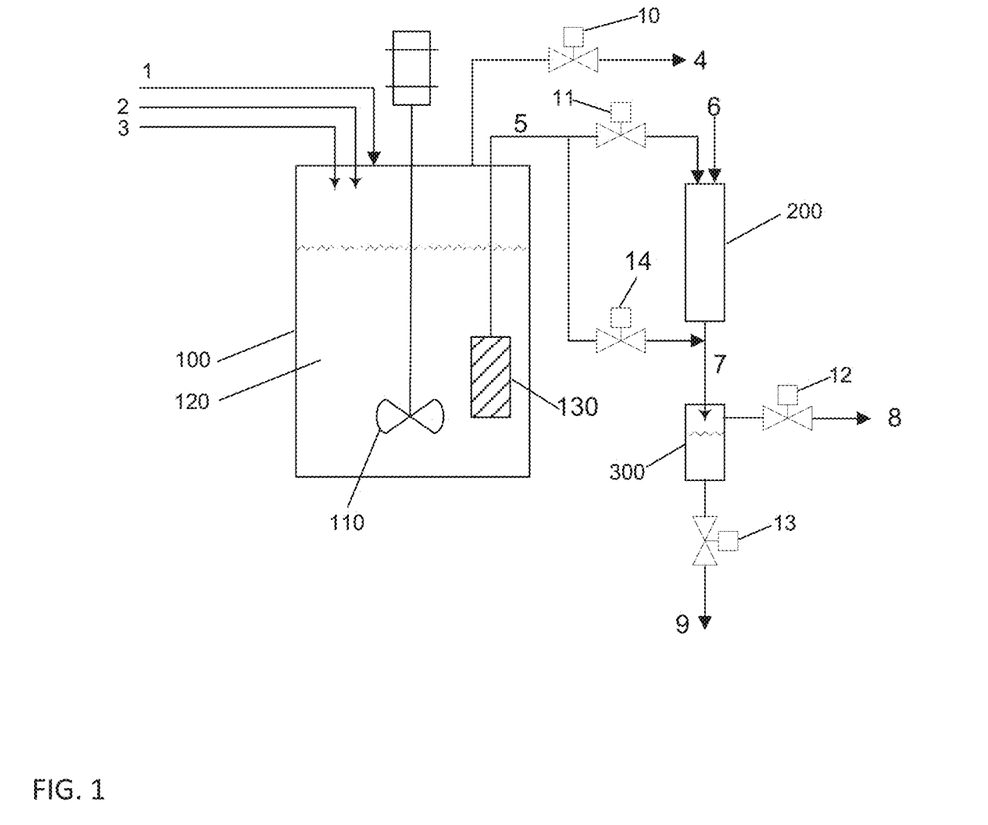
FIG. 1 shows an example process scheme according to an implementation of the disclosed subject matter.

FIG. 1 shows an example process scheme according to an implementation of the disclosed subject matter. An example apparatus and scheme that may be used to perform the conversion of carbohydrate feeds into glycols using a catalyst system comprising a heterogeneous hydrogenation catalyst and a homogeneous tungstate retro-Aldol catalyst, including the acid-treatment conditioning step applied to the hydrogenation catalyst are schematically represented in FIG. 1. As shown in FIG. 1, reactor 100 may be equipped with stirrer 110 and catalyst filter 130. The reactor may also be equipped with automatic controls for the control of reactor temperature, back-pressure, liquid holdup level, and stirrer speed. The feed line 1 may be equipped with a gas flowmeter and may be used to provide a continuous flow of hydrogen gas into the reactor 100. Each of the feed lines 2 and 3 may be used to send liquid or slurry streams into the reactor 100, and may be equipped with a pump and a mass flow meter. The feed lines 2 and 3 may be used to continuously add a solution of lactic acid (or any organic acid) in water, the carbohydrate feed (e.g., a glucose solution or slurry of starch in water), solution of sodium meta-tungstate retro-Aldol catalyst, and optionally an alcoholic solvent to the reactor 100. Optionally, the carbohydrate feed and the tungstate retro-Aldol catalyst may be combined as a single liquid feed stream. Typically, the heterogeneous hydrogenation catalyst may be charged to the reactor 100 at the beginning of the reactor operation. The filter element 130 may be used to retain the heterogeneous hydrogenation catalyst and any precipitated oxides of tungsten (W-oxides) present in the reaction medium 120, while allowing the flow of the liquid product via line 5. The flow of the product stream may be controlled by valve 11. The excess gas present in the reactor 100 may be vented by the use of the back-pressure control valve 10. The vent gas may be vented via stream 4.

Reactor 200 may be a tubular reactor containing a catalyst section in the middle and may be used to complete the hydrogenation of the product. Reactor 200 may be equipped with heater temperature controls and inside thermocouples for measuring the temperature of the catalyst bed. The gas feed line 6 may be equipped with a flowmeter and may be used to continuously feed hydrogen to reactor 200. Line 7 may be an in-line product cooler for cooling down the product mixture. The gas-liquid product effluent passing through line 7 may be set up to flow into a gas/liquid separator vessel 300. Valve 12 may be used to control the back-pressure in vessel 300 and valve 13 may be used to control the liquid level in the vessel 300. The vent gas stream from vessel 300 may be vented via stream 8 and the product may be removed via stream 9.

When reactor 200 is lined up in series with the reactor 100, the valve 14 may be kept closed. The reactor 100 may also be operated in standalone mode by keeping valve 11 closed and allowing the product stream to flow directly to the in-line product cooler line 7, via valve 14. For the purpose of studying the performance of the catalyst system employed for the reactor 100, reactor 200 may or may not be lined up in series; the glycol yields produced in reactor 100 and measured in the product stream 9 are substantially the same in either case.

In the disclosed method for the preparation of ethylene glycol from a carbohydrate-containing feed, the residence time in the reactor vessel of the reaction mixture may be at least 1 minute, at least 2 minutes, and at least 5 minutes. Suitably the residence time in the reactor vessel is no more than 5 hours, no more than 2 hours, and no more than 1 hour. According to an implementation, the average residence time in the reactor is no more than 2 hours.

A feature of the presently disclosed subject matter is the ability to run the reaction for a time period of at least 100 hours. In particular, the disclosed process may include running the reaction for a time period of at least 100 hours with a stable catalyst system.

As shown in the Examples section provided below, the presently disclosed method for producing ethylene glycol from a carbohydrate feed has numerous advantages over the prior art. Because the disclosed subject matter achieves improved catalyst performance, the process results in the selective formation of ethylene glycol over the other glycols, high yields of the total glycols mixture, use of a high-concentration sugar solution as feed to the reactor, while maintaining stable catalyst activity over time. Therefore, the disclosed subject matter provides an improved method suitable for the production of glycols from carbohydrate feeds including a catalyst acid conditioning technique to improve the catalyst performance and stability in the process in order to make the overall glycol production process more economical than processes disclosed previously in the industry.

EXAMPLES

Experimental Apparatus:

The apparatus used to perform the experiments shown in Examples 1 to 10 is schematically represented in FIG. 1. A one-liter Hastelloy-C reactor operating in CSTR (Continuous Stirred Tank Reactor) mode and a 0.3 liter tubular fixed bed hydrogenation reactor set up as shown in FIG. 1 were used to conduct the experiments described in the following 10 examples The reactor (e.g., reaction 200 as shown in FIG. 1) was filled with a nickel-ZrO2 catalyst (with a nickel content of 65% wt) diluted with 1:1 weight 20-mesh SiC particles. The nickel catalyst (217.9 grams) and the SiC particles (241.6 grams) were packed in the 24.5 inch tall catalyst section of the reactor. The catalyst was activated by reduction with flowing $H_2$. The reduction was carried out at a pressure of 50 PSIG and $H_2$ flow rate of 10 standard liters per hour by ramping up the temperature from room temperature to 100° C. over a period of one hour, followed by ramping up the temperature to 250° C. over a period of 2 hours and holding at conditions overnight. At the completion of the reduction procedure, the reactor pressure was raised to 1250 PSIG and kept in standby mode, ready to be lined up in series with the main reactor on demand Example 1

Conversion of 10% wt Glucose Feed Solution

In this example, 30.6 grams of WR Grace Raney®-Ni 2800 (supplied by Aldrich-Sigma Chemical Company) was loaded into the CSTR autoclave vessel. The reactor was pressurized with hydrogen and controlled at 1000 PSIG. The $H_2$ gas flow was set at 25 standard liters per hour. The liquid level control was set at 50% volume. The catalyst was activated and conditioned by the use of a three-step procedure, involving water-washing of the catalyst in the first step at room temperature in the presence of hydrogen at a total reactor pressure of 1000 psig, a reduction procedure in the second step in which the temperature of the reactor was raised to and held at 100° C., and the lactic acid treatment in the third step in which the reactor temperature was raised to and held in the 210 to 230° C. range and the pressure held in the 1000 to 1500 psig range. The water washing step was carried out for a period of 2.8 hours at a rate of 5 ml/min of water flow. The catalyst reduction step at 100° C. was carried out for 18 hours during which the water flow continued. The reactor temperature was then raised to 230° C. before starting the lactic acid solution. The lactic acid feed was a solution of 0.1% wt lactic acid in water. The lactic acid treatment of the catalyst was carried out for a total duration of 36 hours at a flow rate of 5 ml/min At the end of the acid-treatment catalyst conditioning step, the glucose to glycols conversion experiment was started. The feed was a solution containing 10.0% wt glucose and 0.30% wt sodium meta-tungstate in water. At the end of 168 hours of run time, the experiment was concluded by stopping the sugar feed. Product samples were analyzed by HPLC and GC methods, which have been calibrated by the use of standards prepared by the use of pure chemical components. Experimental conditions and the yield results as a function of run time are given in Table 1. The fixed-bed catalyst reactor was kept offline during the entire course of this example.

Example 2

Conversion of 10% wt Glucose Feed Solution

In this example, 30.1 grams of WR Grace Raney®-Ni 2800 was added to the CSTR autoclave vessel, and this example was carried out in a manner similar to Example 1. The reactor was pressurized with hydrogen and controlled at 1000 PSIG. The $H_2$ gas flow was set at 25 standard liters per hour. The catalyst slurry (with liquid volume controlled at 500 ml) was washed with water at a flow rate of 5 ml/min over a period of 6 hours to obtain a final pH (by online pH meter) of 8.5. Further washing and activation of the catalyst was carried out overnight (over a period of 17 hours) at a temperature of 100° C. and a reduced water flow rate of 1 ml/min The reactor temperature was ramped up to 230° C. over a period of one hour. Water flow was stopped, and the 0.1%wt lactic acid feed was started. The acid treatment step was carried out over a period of 24 hours at an acid solution flow rate of 5 ml/min The glucose feed containing 10.00% wt glucose and 0.300% wt sodium meta-tungstate was then started. Experimental conditions and the yield results as a function of run time are given in Table 2. The fixed-bed catalyst reactor was kept offline during the entire course of this example.

Example 3

Conversion of 10% wt Glucose Feed Solution

In this example, 29.2 grams of WR Grace Raney®-Ni 2800 was loaded into the CSTR autoclave vessel, and this example was carried out in a manner similar to Example 1. All three steps of the catalyst activation procedure were carried out at a reactor pressure of 1500 psig. The $H_2$ gas flow was set at 25 standard liters per hour. After performing the catalyst washing and activation steps similar to Example 2, the lactic acid treatment was carried out for a period of 36 hours compared to the 24-hour period in Example 2. A feed solution containing 10.0% wt glucose and 0.30% wt sodium meta-tungstate was then started. Additionally, the Ni—ZrO2 catalyst fixed-bed reactor was lined up in series 4.5 hours after starting up the 10% glucose feed. Experimental conditions and the yield results as a function of run time are given in Table 3.

Example 4

Conversion of 20% wt Glucose Feed Solution

In this example, 30.4 grams of WR Grace Raney®-Ni 2800 was loaded into the CSTR autoclave vessel, and this example was carried out in a manner similar to Example 1. The catalyst was washed with water at room temperature for a 24 hour period at 1500 PSIG reactor pressure, followed by activation at 100° C. for a 28 hour period. The $H_2$ gas flow was set at 25 standard liters per hour. The temperature was then raised to 230° C. and the lactic acid (0.1% wt solution) treatment was carried out for a period of 38 hours. A solution containing 20.0% wt glucose and 0.30% NaMT was used as feed. The solution feed rate to the CSTR reactor (e.g., reactor 100 in FIG. 1) was adjusted to 50% of the rate used in Example-3 in order to maintain the same rate of glucose addition. The fixed-bed reactor (e.g., reactor 200 in FIG. 1) containing the Ni—ZrO2 catalyst was kept offline during the first 26 hours of run time. The reactor was then put online at a temperature of 100° C. and backpressure of 1350 psig. Experimental conditions and the yield results as a function of run time are given in Table 4.

Example 5

Conversion of 20% wt Glucose Feed Solution

In this example, which was a duplicate of Example 4, 29.9 grams of WR Grace Raney®-Ni 2800 was loaded into the CSTR autoclave vessel. The catalyst was washed with water at room temperature for a 22 hour period at 1500 PSIG reactor pressure, followed by activation at 100° C. for a 26 hour period. The temperature was then raised to 230° C. and lactic acid (0.1% wt solution) treatment was carried out for a period of 36 hours. The $H_2$ gas flow was set at 25 standard liters per hour. A feed solution containing 20.0% wt glucose and 0.30% NaMT was used as feed. The fixed-bed reactor containing the Ni—ZrO2 catalyst was kept offline during the first 5 hours of run time. The reactor was then put online at a backpressure of 1350 psig, and the temperature was raised to 125° C. Experimental conditions and the yield results as a function of run time are given in Table 5.

Example 6

Conversion of 10% Glucose—Comparative Example without Lactic Acid Conditioning

This example was carried out by excluding the presently disclosed lactic acid treatment conditioning of the Raney-Ni hydrogenation catalyst.

WR Grace Raney®-Ni 2800, 30.5 grams of the catalyst, was added to the CSTR autoclave vessel. The reactor was pressurized with hydrogen and controlled at 1500 PSIG. The $H_2$ gas flow was set at 25 standard liters per hour. The catalyst slurry (with liquid volume controlled at 500 ml) was washed with water at a flow rate of 5 ml/min over a period of 7 hours to obtain a final pH (by online pH meter) of 8.7 in the reactor effluent. Further washing and activation of the catalyst was carried out overnight (over a period of 17 hours) at a temperature of 100° C. and a reduced water flow rate of 1 ml/min. The reactor temperature was ramped up to 230° C. over a period of one hour; simultaneously the temperature of the fixed-bed catalyst reactor (e.g., reactor 200 in FIG. 1) was ramped up to 50° C. and the pressure was adjusted to 1250 PSIG. Water flow was stopped, the fixed-bed catalyst reactor was lined up to receive the product from the autoclave CSTR, and the glucose feed containing 10.0% wt glucose and 0.30% wt sodium meta-tungstate was then started. During the course of this example, the fixed-bed catalyst reactor conditions were changed in the 20-100° C. temperature range and 1250 to 1400 PSIG pressure range. Other experimental conditions and the yield results as a function of run time are given in Table 6.

Example 7

Conversion of 20% Glucose

In this example, 28.1 grams of WR Grace Raney®-Ni 2800 was loaded into the CSTR autoclave vessel. The reactor was pressurized with hydrogen and controlled at 800 PSIG. The $H_2$ gas flow was set at 25 standard liters per hour. The catalyst slurry (with liquid volume controlled at 500 ml) was washed with water at a flow rate of 10 ml/min over a period of two hours. Further washing and activation of the catalyst was carried out over a period of two hours at a temperature of 100° C. The reactor pressure was increased to 1500 PSIG and the temperature was ramped up to 230° C. over a period of one hour before starting the glucose feed. A solution containing 20.0% wt glucose and 0.30% wt sodium meta-tungstate was used as feed. The glucose feed was started at the target flow rate of 2.5 ml/minute. The fixed-bed catalyst reactor (e.g., reactor 200 in FIG. 1) was kept offline during this run. Experimental conditions and the yield results as a function of run time are given in Table 7.

Example 8

Conversion of 20% Glucose—Comparative Example Showing Effect of Lowered Catalyst Amount In this example, 19.8 grams of WR Grace Raney®-Ni 2800 was loaded into the CSTR autoclave vessel. The reactor was pressurized with hydrogen and controlled at 1250 PSIG. The $H_2$ gas flow was set at 25 standard liters per hour. The catalyst slurry (with liquid volume controlled at 500 ml) was washed with water at a flow rate of 10 ml/min over a period of two hours. Further washing and activation of the catalyst was carried out over a period of two hours at a temperature of 100° C. At the end of the procedure the pH of the reactor effluent was 5.9. The reactor pressure was increased to 1500 PSIG and the temperature was ramped up to 230° C. over a period of one hour before starting the glucose feed. A solution containing 20.0% wt glucose and 0.45% wt sodium meta-tungstate was used as feed. The glucose feed was started at the target flow rate of 2.5 ml/minute. The fixed-bed catalyst reactor (e.g., reactor 200 in FIG. 1) was kept offline during this run. Experimental conditions and the yield results as a function of run time are given in Table 8.

Example 9

Conversion of 20% Glucose—Comparative Example Showing Effect of Lowered Catalyst Amount In this example, 10.4 grams of WR Grace Raney®-Ni 2800 was loaded into the CSTR autoclave vessel. The reactor was pressured up with hydrogen and controlled at 1500 PSIG. The $H_2$ gas flow was set at 25 standard liters per hour. In this example, the water-washing and the catalyst activation steps were combined into a single step. The catalyst slurry (with liquid volume controlled at 500 ml) was washed with water at a flow rate of 7.5 ml/min and the reactor temperature was raised to 100° C. The procedure was completed over a period of 6.5 hours. At the end of the procedure the pH of the reactor effluent was 7.7. The temperature was ramped up to 230° C. over a period of one hour before starting the glucose feed. A solution containing 20.0% wt glucose and 0.45% wt sodium meta-tungstate was used as feed. The glucose feed was started at a target flow rate of 5.0 ml/minute. The fixed-bed catalyst reactor (e.g., reactor 200 in FIG. 1) was kept offline during this run. Experimental conditions and the yield results as a function of run time are given in Table 9.

Example 10

Conversion of 20% Glucose—Comparative Example Showing Effect of Lowered Catalyst Amount In this example, 5.0 grams of WR Grace Raney®-Ni 2800 was loaded into the CSTR autoclave vessel. The reactor was pressured up with hydrogen and controlled at 1500 PSIG. The $H_2$ gas flow was set at 25 standard liters per hour. The catalyst slurry (with liquid volume controlled at 500 ml) was washed with water at a flow rate of 7.5 ml/min over a period of 4 hours. Further washing and activation of the catalyst was carried out over a period of 3.5 hours at a temperature of 100° C. At the end of the procedure the pH of the reactor effluent was 7.4. The temperature was ramped up to 230° C. over a period of one hour before starting the glucose feed. A solution containing 20.0% wt glucose and 0.45% wt sodium meta-tungstate was used as feed. The glucose feed was started at the target flow rate of 5.0 ml/minute. The fixed-bed catalyst reactor was kept offline during this run. Experimental conditions and the yield results as a function of run time are given in Table 10.

Experimental Results:

TABLE 1

Experimental Results from Example 1

| Run Time [Hour] | C3 to C6 Polyols | Wt % Yields of Products | | | Total Glycols |
|---|---|---|---|---|---|
| | | EG | PG | 12BDO | |
| 7.9 | 17.2 | 71.6 | 2.0 | 1.3 | 74.9 |
| 31.8 | 19.6 | 69.9 | 2.2 | 1.3 | 73.3 |
| 71.7 | 20.7 | 66.0 | 2.8 | 1.5 | 70.3 |
| 102.0 | 23.3 | 60.4 | 3.1 | 1.6 | 65.1 |
| 127.4 | 23.1 | 58.0 | 3.3 | 1.8 | 63.1 |
| 167.3 | 23.5 | 54.7 | 3.7 | 2.0 | 60.3 |

Raney-Ni catalyst=30.6 grams, conditioned with lactic acid; reactor pressure=1500 psig; temperature=230° C.; glucose concentration=10.0% wt; sodium meta-tungstate (NaMT) concentration=0.30% wt; liquid feed rate target=5.0 ml /min; C3 to C6 polyols=hydroxy-acetone+glycerol+erythritol+threitol+sorbitol+mannitol; EG=ethylene glycol; PG=propylene glycol; 12BDO=1,2-butanediol.

TABLE 2

Experimental Results from Example 2

| Run Time [Hour] | C3 to C6 Polyols | Wt % Yields of Products | | | Total Glycols |
|---|---|---|---|---|---|
| | | EG | PG | 12BDO | |
| 7.8 | 14.4 | 72.6 | 1.8 | 1.4 | 75.8 |
| 30.9 | 14.7 | 71.0 | 1.9 | 1.6 | 74.5 |

TABLE 2-continued

Experimental Results from Example 2

| Run Time [Hour] | C3 to C6 Polyols | Wt % Yields of Products | | | Total Glycols |
|---|---|---|---|---|---|
| | | EG | PG | 12BDO | |
| 72.0 | 15.9 | 65.0 | 2.4 | 2.0 | 69.3 |
| 101.5 | 13.8 | 63.3 | 2.8 | 2.3 | 68.4 |
| 142.2 | 11.7 | 58.6 | 3.0 | 2.5 | 64.1 |
| 169.9 | 10.4 | 53.8 | 3.2 | 2.5 | 59.6 |

Raney-Ni catalyst=30.1 grams, conditioned with lactic acid; reactor pressure=1500 psig; temperature=230° C.; glucose concentration=10.0% wt; sodium meta-tungstate (NaMT) concentration=0.30% wt; liquid feed rate target=5.0 ml/min; C3 to C6 polyols=hydroxy-acetone+glycerol+erythritol+threitol+sorbitol+mannitol; EG=ethylene glycol; PG=propylene glycol; 12BDO=1,2-butanediol.

TABLE 3

Experimental Results from Example 3

| Run Time [Hour] | C3 to C6 Polyols | Wt % Yields of Products | | | Total Glycols |
|---|---|---|---|---|---|
| | | EG | PG | 12BDO | |
| 8.3 | 11.4 | 74.6 | 3.2 | 2.2 | 80.0 |
| 31.3 | 14.0 | 70.6 | 3.4 | 2.4 | 76.4 |
| 74.7 | 14.1 | 64.1 | 4.1 | 3.2 | 71.3 |
| 101.5 | 14.9 | 59.9 | 4.5 | 3.6 | 67.9 |
| 142.7 | 11.0 | 55.0 | 4.0 | 2.9 | 61.9 |
| 171.5 | 9.7 | 54.3 | 5.4 | 4.4 | 64.1 |

Raney-Ni catalyst=29.2 grams, conditioned with lactic acid; reactor pressure=1500 psig; temperature=230° C.; glucose concentration=10.0% wt; sodium meta-tungstate (NaMT) concentration=0.30% wt; liquid feed rate target=5.0 ml /min; C3 to C6 polyols =hydroxy-acetone+glycerol+erythritol+threitol+sorbitol+mannitol; EG=ethylene glycol; PG=propylene glycol; 12BDO=1,2-butanediol.

TABLE 4

Experimental Results from Example 4

| Run Time [Hour] | C3 to C6 Polyols | Wt % Yields of Products | | | Total Glycols |
|---|---|---|---|---|---|
| | | EG | PG | 12BDO | |
| 10.0 | 15.4 | 68.4 | 1.9 | 1.7 | 72.0 |
| 46.3 | 17.4 | 70.0 | 2.2 | 1.8 | 74.0 |
| 75.3 | 15.4 | 69.2 | 2.6 | 2.2 | 74.0 |
| 118.5 | 15.1 | 60.7 | 3.3 | 3.1 | 67.1 |
| 145.3 | 12.4 | 60.3 | 3.5 | 3.4 | 67.2 |
| 169.5 | 10.6 | 59.0 | 3.6 | 3.5 | 66.1 |

Raney-Ni catalyst=30.4 grams, conditioned with lactic acid; reactor pressure=1500 psig; temperature=230° C.; glucose concentration=20.0% wt; sodium meta-tungstate (NaMT) concentration=0.30% wt; liquid feed rate target=2.5 ml /min; C3 to C6 polyols=hydroxy-acetone+glycerol+erythritol +threitol+sorbitol+mannitol; EG=ethylene glycol; PG=propylene glycol; 12BDO=1,2-butanediol.

TABLE 5

Experimental Results from Example 5

| Run Time [Hour] | C3 to C6 Polyols | Wt % Yields of Products | | | Total Glycols |
|---|---|---|---|---|---|
| | | EG | PG | 12BDO | |
| 11.4 | 17.8 | 65.0 | 2.0 | 1.7 | 68.7 |
| 47.7 | 19.0 | 68.2 | 2.5 | 1.8 | 72.5 |
| 87.1 | 19.8 | 62.7 | 2.7 | 2.3 | 67.6 |
| 116.4 | 13.0 | 67.5 | 3.0 | 2.6 | 73.1 |
| 143.1 | 11.9 | 66.7 | 3.2 | 2.9 | 72.7 |
| 183.2 | 10.6 | 63.6 | 3.8 | 3.3 | 70.6 |

Raney-Ni catalyst=29.9 grams, conditioned with lactic acid; reactor pressure=1500 psig; temperature=230° C.; glucose concentration=20.0% wt; sodium meta-tungstate (NaMT) concentration=0.30% wt; liquid feed rate target=2.5 ml /min; C3 to C6 polyols=hydroxy-acetone+glycerol+erythritol +threitol+sorbitol+mannitol; EG=ethylene glycol; PG=propylene glycol; 12BDO=1,2-butanediol.

TABLE 6

Experimental Results from Example 6

| Run Time [Hour] | C3 to C6 Polyols | Wt % Yields of Products | | | Total Glycols |
|---|---|---|---|---|---|
| | | EG | PG | 12BDO | |
| 7.1 | 45.2 | 27.9 | 4.0 | 1.3 | 33.2 |
| 31.2 | 50.8 | 23.0 | 5.5 | 1.5 | 29.9 |
| 49.8 | 48.7 | 23.5 | 5.4 | 1.5 | 30.4 |
| 71.4 | 45.5 | 26.0 | 4.8 | 1.6 | 32.3 |
| 78.0 | 44.1 | 26.6 | 4.6 | 1.5 | 32.6 |
| 101.3 | 44.5 | 29.4 | 4.6 | 1.5 | 35.4 |

Raney-Ni catalyst=30.5 grams; reactor pressure=1500 psig; temperature=230° C.; glucose concentration=10.0% wt; sodium meta-tungstate (NaMT) concentration=0.30% wt; liquid feed rate target=5.0 ml /min; $C_3$ to $C_6$ polyols=hydroxy-acetone+glycerol+erythritol+threitol+sorbitol+mannitol; EG=ethylene glycol; PG=propylene glycol; 12BDO=1,2-butanediol.

TABLE 7

Experimental Results from Example 7

| Run Time [Hour] | Exptl Conditions | | Wt % Yields of Products | | | | Total Glycols |
|---|---|---|---|---|---|---|---|
| | Feed Soln [G/min] | NaMT [Wt %] | C3 to C6 Polyols | EG | PG | 12BDO | |
| 22.9 | 2.56 | 0.30 | 42.0 | 36.1 | 5.1 | 1.5 | 42.6 |
| 54.5 | 2.56 | 0.30 | 40.2 | 36.3 | 5.3 | 1.6 | 43.1 |
| 70.7 | 5.04 | 0.30 | 46.8 | 33.7 | 4.3 | 1.5 | 39.4 |
| 73.5 | 5.04 | 0.30 | 46.1 | 32.8 | 4.2 | 1.5 | 38.4 |
| 79.2 | 4.81 | 0.45 | 41.2 | 38.7 | 4.1 | 1.5 | 44.3 |
| 117.5 | 4.81 | 0.45 | 34.7 | 40.8 | 4.6 | 1.7 | 47.1 |
| 146.5 | 5.02 | 0.45 | 15.8 | 9.2 | 1.8 | 0.9 | 11.8 |

Raney-Ni catalyst=28.1 grams; reactor pressure=1500 psig; temperature=230° C.; glucose concentration=20.0% wt; sodium meta-tungstate (NaMT) concentration=0.30 to 0.45% wt; liquid feed rate target=2.5 to 5.0 ml /min; C3 to C6 polyols=hydroxy-acetone+glycerol+erythritol+threitol+sorbitol+mannitol; EG=ethylene glycol; PG=propylene glycol; 12BDO=1,2-butanediol.

TABLE 8

Experimental Results from Example 8

| Run Time [Hour] | Experimental Conditions | | | Wt % Yields of Products | | | | Total Glycols |
|---|---|---|---|---|---|---|---|---|
| | Press [PSIG] | Feed Soln [G/min] | NaMT [Wt %] | C3 to C6 Polyols | EG | PG | 12BDO | |
| 22.8 | 1500 | 2.51 | 0.45 | 40.7 | 40.3 | 5.0 | 1.4 | 46.6 |
| 31.0 | 1500 | 5.11 | 0.45 | 42.7 | 40.2 | 3.7 | 1.3 | 45.2 |
| 46.7 | 1500 | 5.11 | 0.45 | 39.8 | 42.0 | 3.7 | 1.5 | 47.2 |
| 51.8 | 1200 | 5.11 | 0.45 | 31.5 | 49.2 | 4.3 | 1.6 | 55.1 |
| 55.3 | 1200 | 5.11 | 0.45 | 32.3 | 48.4 | 4.2 | 1.6 | 54.2 |
| 73.3 | 1200 | 5.12 | 0.60 | 8.9 | 5.2 | 2.2 | 1.0 | 8.3 |

Raney-Ni catalyst=19.8 grams; reactor pressure=1200 to 1500 psig; temperature=230° C.; glucose concentration=20.0% wt; sodium meta-tungstate (NaMT) concentration=0.45 to 0.60% wt; liquid feed rate target=2.5 to 5.0 ml /min; C3 to C6 polyols=hydroxy-acetone+glycerol+erythritol+threitol+sorbitol+mannitol; EG=ethylene glycol; PG=propylene glycol; 12BDO=1,2-butanediol.

TABLE 9

Experimental Results from Example 9

| Run Time [Hour] | Press [PSIG] | Wt % Yields of products | | | | Total Glycols |
|---|---|---|---|---|---|---|
| | | C3 to C6 Polyols | EG | PG | 12BDO | |
| 8.7 | 1500 | 30.9 | 52.2 | 3.0 | 1.5 | 56.6 |
| 25.1 | 1500 | 31.2 | 52.8 | 3.3 | 1.5 | 57.6 |
| 43.4 | 1500 | 30.5 | 52.4 | 3.7 | 1.6 | 57.6 |
| 66.5 | 1500 | 28.7 | 51.2 | 3.9 | 1.8 | 57.0 |
| 68.7 | 1200 | 18.6 | 40.8 | 3.5 | 1.8 | 46.1 |
| 70.7 | 1500 | 10.0 | 18.1 | 3.4 | 2.0 | 23.5 |

Raney-Ni catalyst=10.4 grams; reactor pressure=1200 to 1500 psig; temperature =230° C.; glucose concentration=20.0% wt; sodium meta-tungstate (NaMT) concentration =0.45% wt; liquid feed rate target=5.0 ml /min; C3 to C6 polyols=hydroxy-acetone +glycerol+erythritol +threitol+sorbitol+mannitol; EG=ethylene glycol; PG=propylene glycol; 12BDO=1,2-butanediol.

TABLE 10

Experimental Results from Example 10

| Run Time [Hour] | C3 to C6 Polyols | Wt % Yields of Products | | | Total Glycols |
|---|---|---|---|---|---|
| | | EG | PG | 12BDO | |
| 4.8 | 17.8 | 52.8 | 3.1 | 1.9 | 57.8 |
| 7.1 | 14.2 | 46.6 | 3.9 | 2.5 | 53.0 |
| 9.5 | 14.4 | 24.2 | 2.4 | 1.5 | 28.1 |
| 10.8 | 13.5 | 28.7 | 3.8 | 2.4 | 34.9 |
| 11.8 | 11.4 | 26.9 | 3.9 | 2.5 | 33.2 |

Raney-Ni catalyst=5.0 grams; reactor pressure=1500 psig; temperature=230° C.; glucose concentration=20.0% wt; sodium meta-tungstate (NaMT) concentration=0.45% wt; liquid feed rate target=5.0 ml /min; C3 to C6 polyols=hydroxy-acetone+glycerol+erythritol+threitol+sorbitol+mannitol; EG=ethylene glycol; PG=propylene glycol; 12BDO=1,2-butanediol.

Analysis of Results from Examples 1-10:

In Example 1, as part of the catalyst activation procedure, the Raney®-nickel hydrogenation catalyst was conditioned by treating with lactic acid solution under the typical reactor operating conditions of $H_2$ pressure and temperature. The concentration of the glucose feed used in this example was 10.0% wt and the sodium meta-tungstate (NaMT) concentration was 0.030% wt. The experimental results obtained from Example 1 are shown in Table 1 above. Additional Examples, specifically Examples 2 to 5, show the utility of the presently disclosed lactic acid conditioning of the catalyst as shown in Tables 2 to 5. In all of the Examples the conditioned catalyst provided superior yields of the desired glycols and improved catalyst stability (i.e. long run times) compared to Example 6 which was carried out by omitting the lactic acid conditioning step of the catalyst activation procedure.

In Example 1, a total glycols yield of 75% was obtained initially, and the yield was still high when the experiment was terminated at the end of 167 hours. As shown by Examples 2 and 3, these superior results can be reproduced more than once indicating that the lactic acid conditioning procedure is a highly reliable means by which the desired outcomes, improved glycols yield and reaction run time, can be realized. In Examples 4 and 5, a 20% wt glucose feed was used to demonstrate that higher concentrations of glycols can be produced in the reaction mixture as a result of the lactic acid conditioning procedure according to the presently disclosed subject matter. As can be seen in Tables 4 and 5 above, and in comparison with the results shown in Tables 1-3 above, substantially the same catalyst productivity is obtained by doubling the glucose feed concentration from 10 to 20% wt. This demonstrated production of the desired glycols in higher concentrations in the reaction mixture, without sacrificing the yields or the catalyst run time, helps to save energy in the product separation and purification steps thus making the process more economical.

In Example 6, which was carried out by omitting the presently disclosed lactic acid conditioning step of the hydrogenation catalyst activation procedure, the total glycols yield was in the 30 to 35% wt range. Higher yield of the C3 to C6 polyols (in the 44 to 51% wt range) was produced compared to Examples 1 to 5 but these products are not desirable. In Example 7, the effects of feed rate addition and the sodium meta-tungstate retro-Aldol catalyst concentration were examined As can be seen from the results shown in Table 7 above, the glycol yields were still low and the polyols production was relatively high. In both of the Examples 6 and 7, compared to the previous Examples 1 to 5, the shift in yields from glycols to polyols (i.e. less glycols and more polyols) may be characterized as due to a higher level of activity of the hydrogenation catalyst relative to the activity of the tungstate retro-Aldol catalyst. Examples 8 to 10 were performed by a step-wise decrease in the amount of Raney®-Ni catalyst initially loaded to the CSTR reactor, from the typical 30 grams charge to 19.8 grams in Example 8, 10.4 grams in Example 9, and 5 grams in Example 10. As can be seen from the results shown in Tables 8 to 10 above, the total glycol yields were less than the minimum target of 60%. Additionally, the catalyst life times are relatively shorter with decreasing amounts of the Raney®-Ni catalyst used for the reaction. In Example 10, the catalyst lasted only for a period of 12 hours, at the end of which time unacceptable levels of glucose decomposition was observed and the reactor became inoperable.

Figure 2:
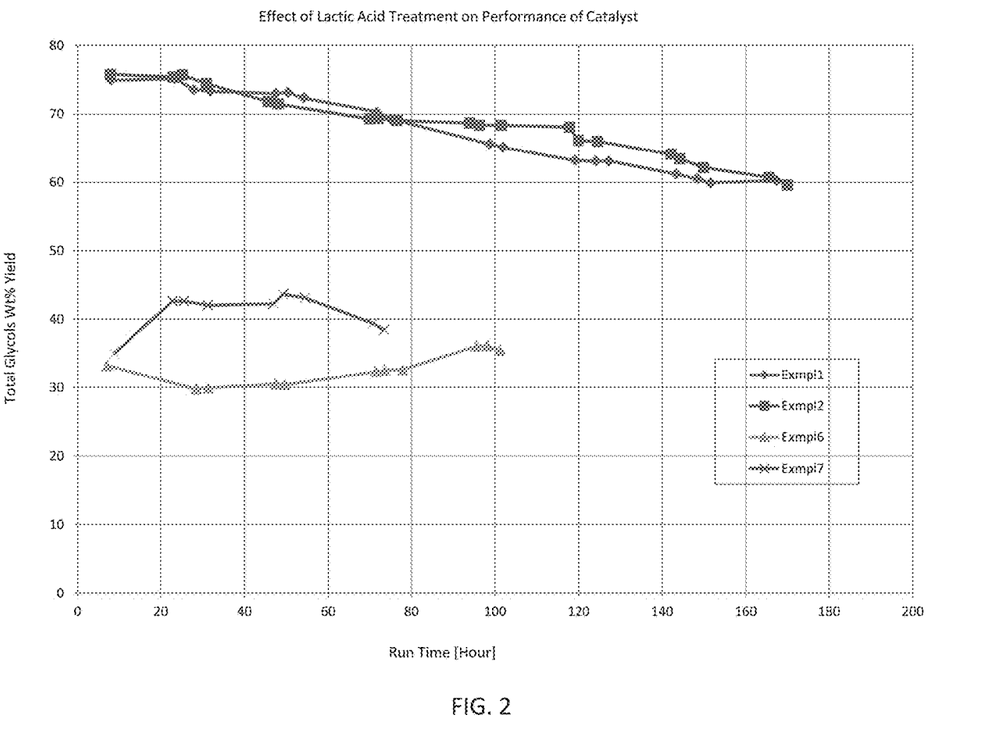
FIG. 2 shows examples of the effect of acid treatment on catalyst performance in the process scheme according to an implementation of the disclosed subject matter.

FIG. 2 shows the effect of the catalyst conditioning step on the performance of the catalyst system according to embodiments of the presently disclosed subject matter. The total glycol yield data from Examples 1, 2, 6, and 7 are graphically shown in FIG. 2 in which the yields are plotted as a function of experimental run time. The performance difference between the hydrogenation catalyst that has been conditioned with lactic acid (Examples 1 and 2) and the unconditioned catalyst (Examples 6 and 7) can be clearly visualized.

All of the above examples clearly show, with a very high degree of certainty, the utility of the lactic acid conditioning method of activating the hydrogenation catalyst used in the carbohydrates to glycols process.

As shown in the Examples section above, the presently disclosed method for producing ethylene glycol from a carbohydrate feed has numerous advantages over the prior art. Because the disclosed subject matter achieves improved catalyst performance, the process results in the selective formation of ethylene glycol over the other glycols, high yields of the total glycols mixture, use of a high-concentration sugar solution as feed to the reactor, while maintaining stable catalyst activity over long run times. Therefore, the disclosed subject matter provides an improved method suitable for the production of glycols from carbohydrate feeds including a catalyst acid conditioning technique to improve the catalyst performance and stability in the process in order to make the overall glycol production process more economical than processes disclosed previously in the industry.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

That which is claimed is:

1. A method for producing ethylene glycol from a carbohydrate feed comprising:
   a) conditioning a heterogeneous hydrogenation catalyst by treatment with a protic acid for a first period of time resulting in an acid-conditioned heterogeneous hydrogenation catalyst;
   b) next, in a first reactor under hydrogenation conditions, the carbohydrate feed is contacted for a second period of time, with the carbohydrate feed with a bi-functional catalyst system comprising:
      1) the acid-conditioned heterogeneous hydrogenation catalyst, and
      2) a soluble retro-Aldol catalyst;
   c) obtaining an intermediate product stream, from the first reactor, comprising ethylene glycol,
   wherein the second period of time follows the first period of time.

2. The method of claim 1, wherein the protic acid is at least one selected from the group consisting of: organic acid, mineral acid, and combinations thereof.

3. The method of claim 2, wherein the organic acid is at least one selected from the group consisting of: formic acid, acetic acid, propionic acid, butyric acid, glycolic acid, lactic acid, citric acid, benzoic acid, and combinations thereof.

4. The method of claim 3, wherein the organic acid is at least one selected from the group consisting of: lactic acid, glycolic acid, and combinations thereof.

5. The method of claim 2, wherein the mineral acid is at least one selected from the group consisting of: HCl, $H_2SO_4$, $H_3PO_4$, benzene sulfonic acid and combinations thereof.

6. The method of claim 1, wherein the conditioning step (a) is carried out with a concentration of protic acid in the range of from 0.001 wt % to 50 wt %.

7. The method of claim 1, wherein the conditioning step (a) is carried out with an acid solution solvent selected from the group consisting of: $H_2O$, alcohol, and combinations thereof.

8. The method of claim 1, wherein the heterogeneous hydrogenation catalyst comprises at least one selected from the group consisting of: Raney-Ni, Raney-Co, Raney-Cu, Raney-Ru, Ni, Co, Cu, Cu—Zn, Cu—Cr, Ni—Mo, Ni—W, and Ni—Cr.

9. The method of claim 1, wherein the heterogeneous hydrogenation catalyst is further promoted with one or more selected from the group consisting of: Al, Fe, Cr, Mn, Co, Cu, Mo, Ru, Rh, Pd, Ag, W, Re, Ir, Pt, Au, In, Sn, Sb, and Pb.

10. The method of claim 1, wherein the heterogeneous hydrogenation catalyst comprises Raney-Ni.

* * * * *